United States Patent
Wiley et al.

(10) Patent No.: US 12,327,355 B2
(45) Date of Patent: Jun. 10, 2025

(54) SYSTEM AND METHOD FOR GENERATING A DIAGNOSTIC MODEL AND USER INTERFACE PRESENTATION BASED ON INDIVIDUAL ANATOMICAL FEATURES

(71) Applicant: STRATOVAN CORPORATION, Davis, CA (US)

(72) Inventors: David Wiley, Davis, CA (US); Nathan Wetzel, Kennewick, WA (US); Cory Hatcher, Kennewick, WA (US)

(73) Assignee: Stratovan Corporation, Davis, CA (US)

( * ) Notice: Subject to any disclaimer, the term of this patent is extended or adjusted under 35 U.S.C. 154(b) by 329 days.

(21) Appl. No.: 17/863,330

(22) Filed: Jul. 12, 2022

(65) Prior Publication Data

US 2024/0020827 A1    Jan. 18, 2024

(51) Int. Cl.
| | |
|---|---|
| *G06T 7/00* | (2017.01) |
| *G06V 10/26* | (2022.01) |
| *G06V 10/74* | (2022.01) |
| *G06V 10/764* | (2022.01) |
| *G06V 10/771* | (2022.01) |
| *G16H 30/20* | (2018.01) |
| *G16H 50/50* | (2018.01) |

(52) U.S. Cl.
CPC ............ *G06T 7/0012* (2013.01); *G06V 10/26* (2022.01); *G06V 10/761* (2022.01); *G06V 10/764* (2022.01); *G06V 10/771* (2022.01); *G16H 30/20* (2018.01); *G06T 2207/30036* (2013.01); *G16H 50/50* (2018.01)

(58) Field of Classification Search
None
See application file for complete search history.

(56) References Cited

U.S. PATENT DOCUMENTS

| | | | |
|---|---|---|---|
| 2002/0037489 A1* | 3/2002 | Jones | A61C 9/0046 433/213 |
| 2002/0072027 A1* | 6/2002 | Chishti | A61C 7/00 433/24 |
| 2019/0147666 A1* | 5/2019 | Keustermans | G06T 19/20 433/213 |
| 2021/0110605 A1* | 4/2021 | Haslam | G06T 7/11 |

* cited by examiner

*Primary Examiner* — Leon Flores
(74) *Attorney, Agent, or Firm* — Foley & Lardner LLP

(57) ABSTRACT

Example implementations also include a method of generating a diagnostic model and user interface presentation based on individual anatomical features, by generating a distance associated with a subset of anatomical features, characterizing the anatomical features based on one or more feature metrics, generating one or more diagnostic language objects based on one or more diagnostic language metrics, segmenting one or more of the anatomical features based on a diagnostic template, embedding one or more of the segments anatomical features in the diagnostic template, and modifying at least one of the diagnostic language objects, in response to a determination that the diagnostic language object is associated with a separate branch of the tree from another one of the diagnostic language objects.

20 Claims, 12 Drawing Sheets

SYSTEM AND METHOD FOR GENERATING A DIAGNOSTIC MODEL AND USER INTERFACE PRESENTATION BASED ON INDIVIDUAL ANATOMICAL FEATURES

TECHNICAL FIELD

The present implementations relate generally to biomedical imaging, and more particularly to generating a diagnostic model and user interface presentation based on individual anatomical features.

BACKGROUND

Biomedical imaging requires increasing complex biomedical data input and computational processing to achieve successful medical outcomes. Conventional systems may not effectively process biomedical imaging information with sufficient speed and at sufficient granularity to support individualized patient care.

SUMMARY

A technological solution for generating a diagnostic model and user interface presentation based on individual anatomical features is provided.

A method of generating a diagnostic model and user interface presentation based on individual anatomical features can include generating a distance associated with a subset of anatomical features, characterizing the anatomical features based on one or more feature metrics, generating one or more diagnostic language objects based on one or more diagnostic language metrics, segmenting one or more of the anatomical features based on a diagnostic template, embedding one or more of the segments anatomical features in the diagnostic template, and modifying at least one of the diagnostic language objects, in response to a determination that the diagnostic language object is associated with a separate branch of the tree from another one of the diagnostic language objects.

BRIEF DESCRIPTION OF THE DRAWINGS

These and other aspects and features of the present implementations will become apparent to those ordinarily skilled in the art upon review of the following description of specific implementations in conjunction with the accompanying figures, wherein.

DETAILED DESCRIPTION

Figure 1A:
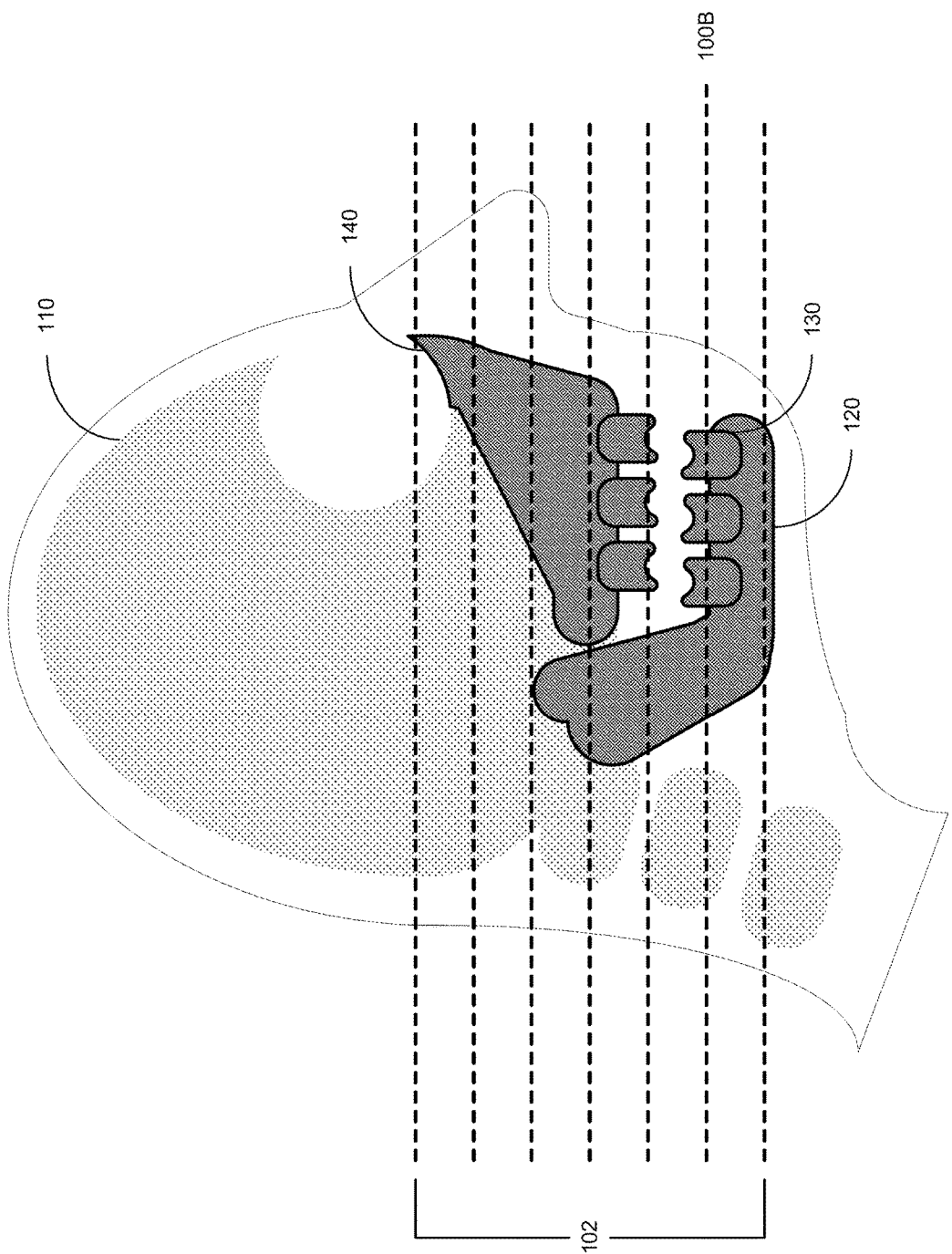
FIG. 1A illustrates an object model including a plurality of object layers, in accordance with present implementations.

The present implementations will now be described in detail with reference to the drawings, which are provided as illustrative examples of the implementations so as to enable those skilled in the art to practice the implementations and alternatives apparent to those skilled in the art. Notably, the figures and examples below are not meant to limit the scope of the present implementations to a single implementation, but other implementations are possible by way of interchange of some or all of the described or illustrated elements. Moreover, where certain elements of the present implementations can be partially or fully implemented using known components, only those portions of such known components that are necessary for an understanding of the present implementations will be described, and detailed descriptions of other portions of such known components will be omitted so as not to obscure the present implementations. Implementations described as being implemented in software should not be limited thereto, but can include implementations implemented in hardware, or combinations of software and hardware, and vice-versa, as will be apparent to those skilled in the art, unless otherwise specified herein. In the present specification, an implementation showing a singular component should not be considered limiting; rather, the present disclosure is intended to encompass other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present implementations encompass present and future known equivalents to the known components referred to herein by way of illustration.

Present implementations can provide an efficient, integrated environment for an oral maxillofacial radiologist to capture information relevant to their diagnostic written report. Present implementations can include a workflow to move a radiologist through an entire scan volume ensuring each anatomical region in the oral maxillofacial complex is reviewed.

Present implementations can, at a user interface, identify and characterize anatomical features within the oral maxillofacial region and embed pre-formatted diagnostic language objects associated with particular anatomical features of the maxillofacial region into a user interface object associated with a diagnostic template, model, or the like. The user interface can include one or more embedded regions, editable regions, or the like, operable to receive input from multiple users on a distributed basis from multiple user devices. As one example, radiologists can collaborate and iterate on diagnostic instructions or modifications input to the user interface object, in the form of diagnostic language objects. These diagnostic language objects can be integrated into the system in accordance with present implementations to advantageously improve speed and accuracy of the identification of anatomical features and generation of diagnostic modification instructions associated therewith. Diagnostic language objects can include predefined diagnostic language objects corresponding to particular diagnostic modifications. As one example, predefined diagnostic language objects can describe most common findings for each anatomical region segmented by the system for diagnostic modification generation. Predefined diagnostic language objects can indicate each possible outcome associated with one or more possible diagnostic modifications to the anatomical feature. Thus, the generation and availability of one or more diagnostic modification and presentation by corresponding diagnostic language objects can advantageously enable, for example, a radiologist to adjust any pre-populated phrases to better match a patient anatomical feature structure. A user interface presentation in accordance with present implementations can present a user interface object with dynamically formatting image types for embedded objects within the diagnostic template.

Present implementations can generate a user interface presentation based at least partially on a tree structure corresponding to dependencies, similarities, or compatibilities, for example, between various diagnostic modifications. The tree structure can include a decision tree or an operation tree, for example, corresponding to particular decision or operations associated with a diagnostic modification. The tree structure can indicate whether particular diagnostic modifications are mutually exclusive. As one example, operations in separate subtrees can be mutually exclusive.

Present implementations can interface with or include one or more processing system and computing systems. An IPS system or an automated CBCT image extraction process, for example, can capture key images for the diagnostic template. An IPS system or an automated CBCT analysis, for example, process can provide dentition charting automatically integrated within the report. An IPS system or an automated CBCT image extraction process, for example, can integrate one or more quantitative characteristics of a model associated with a patient maxillofacial model into descriptive text objects. The quantitative characteristics of a model can include asymmetry analysis, an airway dimension, a mandible width, or a maxilla width.

Present implementations can import patient and case specific details. Present implementations can include user interface presentation objects including image, measurement, and descriptive text components embedded into a diagnostic template based on a clinical purpose of the scan.

FIG. 1A illustrates an object model including a plurality of object layers, in accordance with present implementations. As illustrated by way of example in FIG. 1A, an example object model 100A can include an object model source 110, a first maxillofacial structure 120, anatomical features 130, a second maxillofacial structure, and a plurality of object layers 102 including object layer 100B.

The object model source 110 is or includes one or more 2D images associated with a patient and combined into a 3D model for that patient. In some implementations, the object model source 110 includes multiple Digital Imaging and Communications in Medicine (DICOM) images. In some implementations, the object model source 110 is presented as a 2D projection on a predetermined plane through the 3D model associated with the patient. As one example, a predetermined plane can be a transverse plane, a coronal plane, or a sagittal plane dividing or bisecting the 3D model. In some implementations, the landmarks 120 can be projected onto the predetermined plane to present the landmarks relative to a particular 2D image of the object model source 110.

The first maxillofacial structure can include a mandible, the second maxillofacial structure can include a cranial plate, and the anatomical features can include dentition structure including but not limited to individual teeth.

Figure 1B:
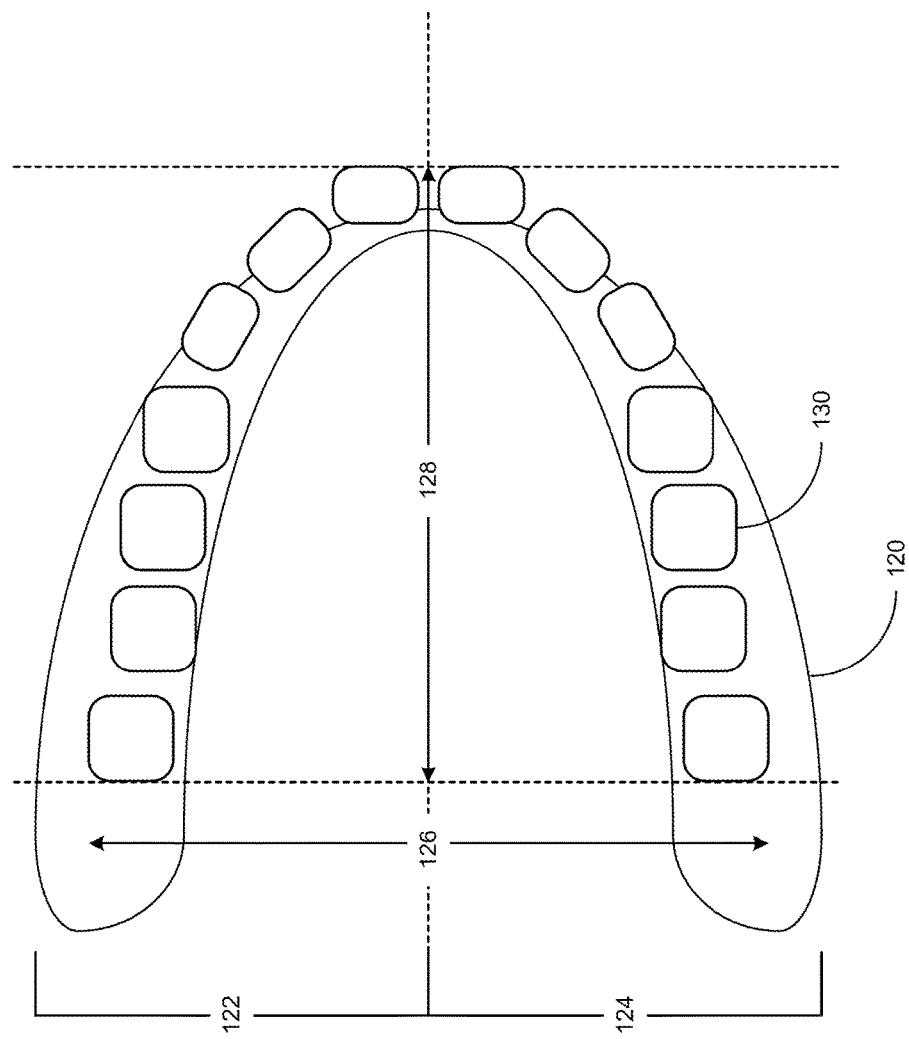
FIG. 1B illustrates an object layer of an object model, further to the object model of FIG. 1A.

FIG. 1B illustrates an object layer of an object model, further to the object model of FIG. 1A. As illustrated by way of example in FIG. 1B, an object layer 100B can include the maxillofacial structure 120, the anatomical structure 130, a first symmetry region 122, a second symmetry region 124, a first maxillofacial structure dimension 126 and a second maxillofacial structure dimension 128. At least one of the systems of FIGS. 4 and 5 can generate one or more of the first maxillofacial structure dimension 126 and the second maxillofacial structure dimension 128. The first symmetry region 122, and the second symmetry region 124 can respectively correspond to right and left portions of the maxillofacial structure.

Figure 2A:
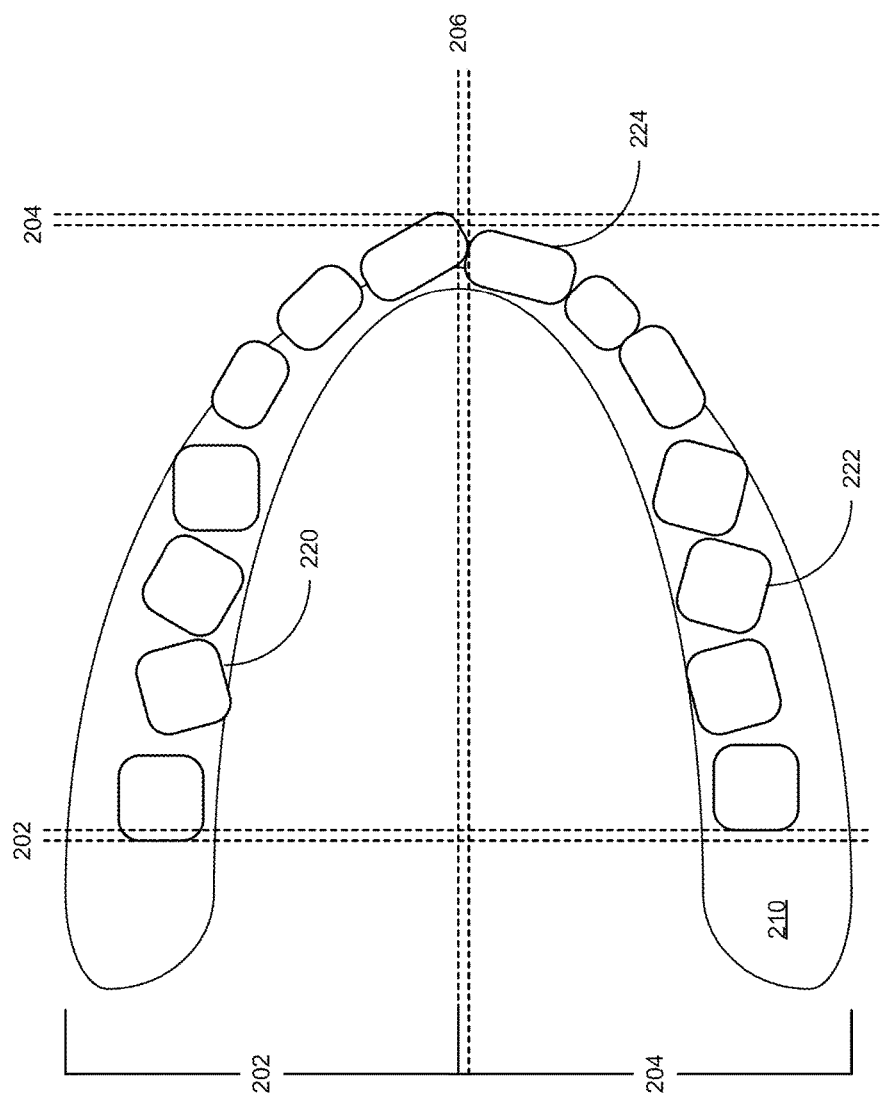
FIG. 2A illustrates a first state an object layer of an object model, in accordance with present implementations.

FIG. 2A illustrates a first state an object layer of an object model, in accordance with present implementations. As illustrated by way of example in FIG. 2A, an example a first state an object layer 200A can include a maxillofacial structure 210, anatomical structures 220, 222 and 224, a first symmetry region 202, a second symmetry region 204, a first anatomical symmetry dimension 202, a second anatomical symmetry dimension 204, and a third anatomical symmetry dimension 206. The first anatomical symmetry dimension 202 can correspond to a difference in position of at least one surface of two corresponding anatomical features at the rear of the maxillofacial structure. The second anatomical symmetry dimension 204 can correspond to a difference in position of at least one surface of two corresponding anatomical features at the front of the maxillofacial structure. The third anatomical symmetry dimension 206 can correspond to a difference in position of at least one surface of two corresponding anatomical features along a center of the maxillofacial structure corresponding to a line between the first symmetry region 202 and the second symmetry region 204. At least one of the systems of FIGS. 4 and 5 can generate one or more of the dimensions 202, 204 and 206. These dimensions can correspond to global distances.

Figure 2B:
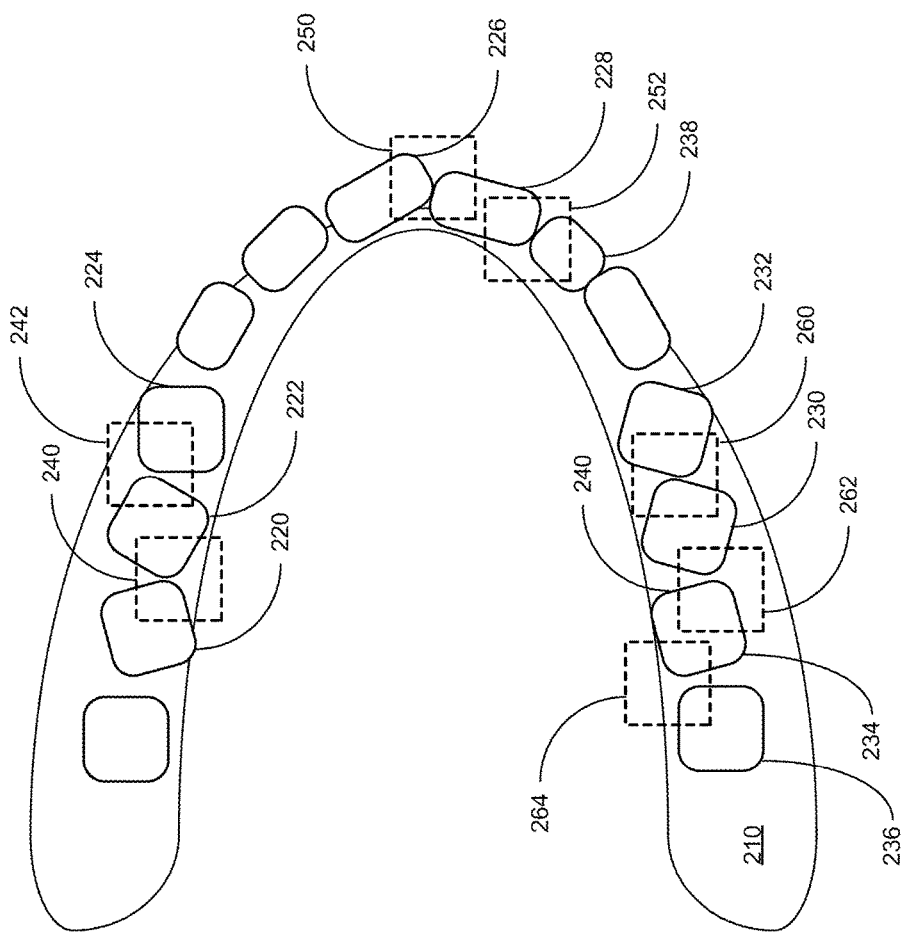
FIG. 2B illustrates a second state an object layer of an object model, in accordance with present implementations.

FIG. 2B illustrates a second state an object layer of an object model, in accordance with present implementations. As illustrated by way of example in FIG. 2B, a second state an object layer 200B can include the maxillofacial structure 210, anatomical structures 220, 222, 224, 226, 228, 230, 232, 234, 236 and 238, and segments 240, 242, 250, 252, 260, 262 and 264. The anatomical structures 220, 222, 224, 226, 228, 230, 232, 234, 236 and 238 can correspond to teeth, for example, each having a particular position and orientation with respect to the maxillofacial structure 210 and its neighboring teeth. The segments 240, 242, 250, 252, 260, 262 and 264 can correspond to portions of the object layer in which one or more anatomical features satisfy one or more feature metrics. A feature metric can indicate, for example, that a position or orientation of tooth is within a predetermined threshold distance of another tooth or away from an ideal position or orientation of the tooth. The segments can correspond to portions of the object layer 200A, and can include images models, or the like. At least one of the systems of FIGS. 4 and 5 can generate one or more of the anatomical structures 220, 222, 224, 226, 228, 230, 232, 234, 236 and 238, and segments 240, 242, 250, 252, 260, 262 and 264, and can identify one or more of the segments based on the feature metrics.

Figure 3A:
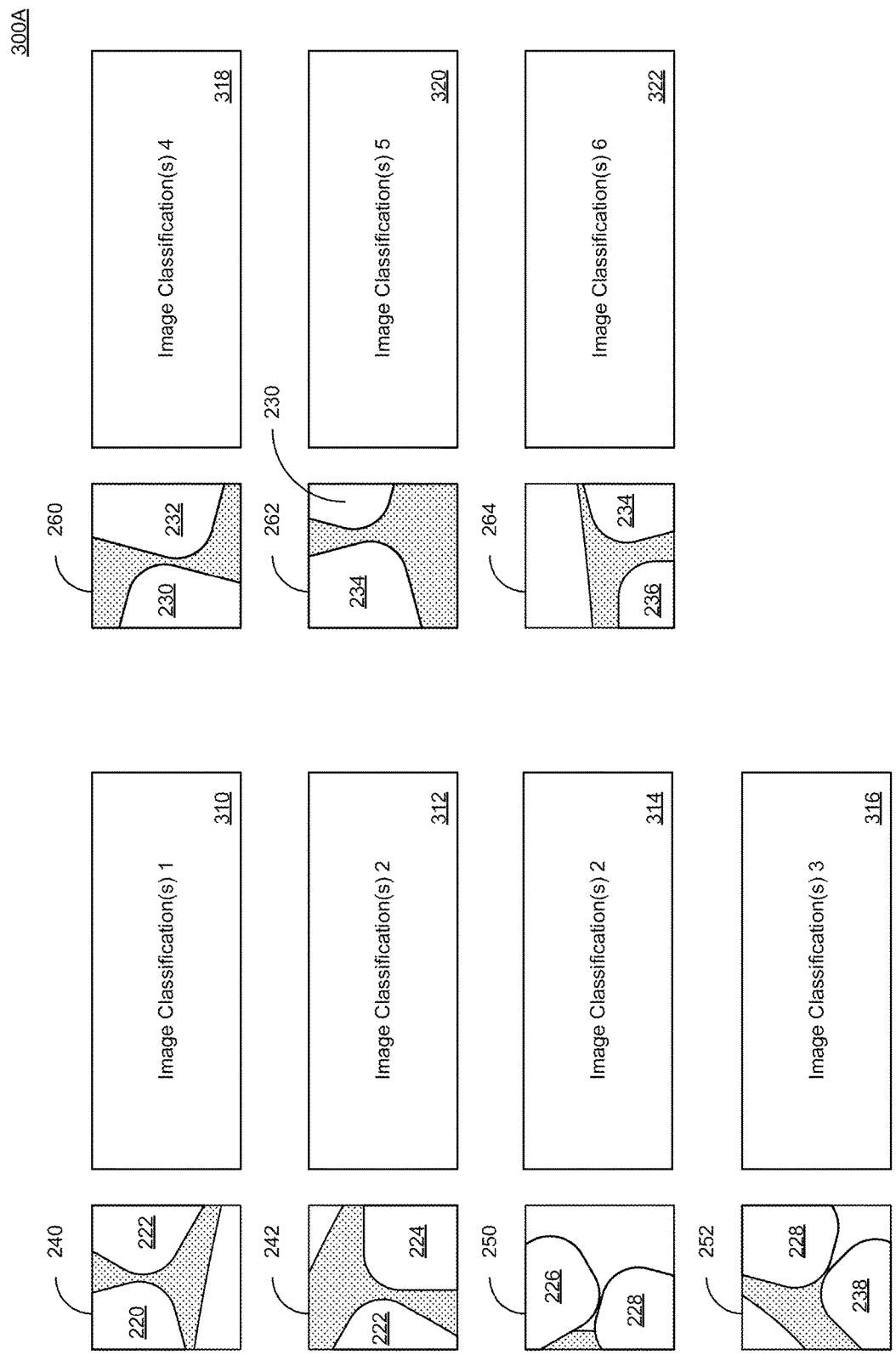
FIG. 3A illustrates a first user interface presentation based on an object layer of an object model, in accordance with present implementations.

FIG. 3A illustrates a first user interface presentation based on an object layer of an object model, in accordance with present implementations. As illustrated by way of example in FIG. 3A, a user interface presentation 300A can include the segments 240, 242, 250, 252, 260, 262 and 264 each including at least portions of various ones of the anatomical structures 220, 222, 224, 226, 228, 230, 232, 234, 236 and 238. The user interface presentation 300A can also include one or more diagnostic language portions 310, 312, 314, 316, 318, 320 and 322. The user interface presentation 300A can be a diagnostic template including embedded regions corresponding to the locations of the segments 240, 242, 250, 252, 260, 262 and 264 and the diagnostic language portions 310, 312, 314, 316, 318, 320 and 322. Each of the diagnostic language portions 310, 312, 314, 316, 318, 320 and 322 can include text or numerical output, for example, classifying a position orientation, interference, or the like, for example, between anatomical structures in each segment or of a particular anatomical structure. At least one of the systems of FIGS. 4 and 5 can generate the user interface presentation 300A.

Figure 3B:
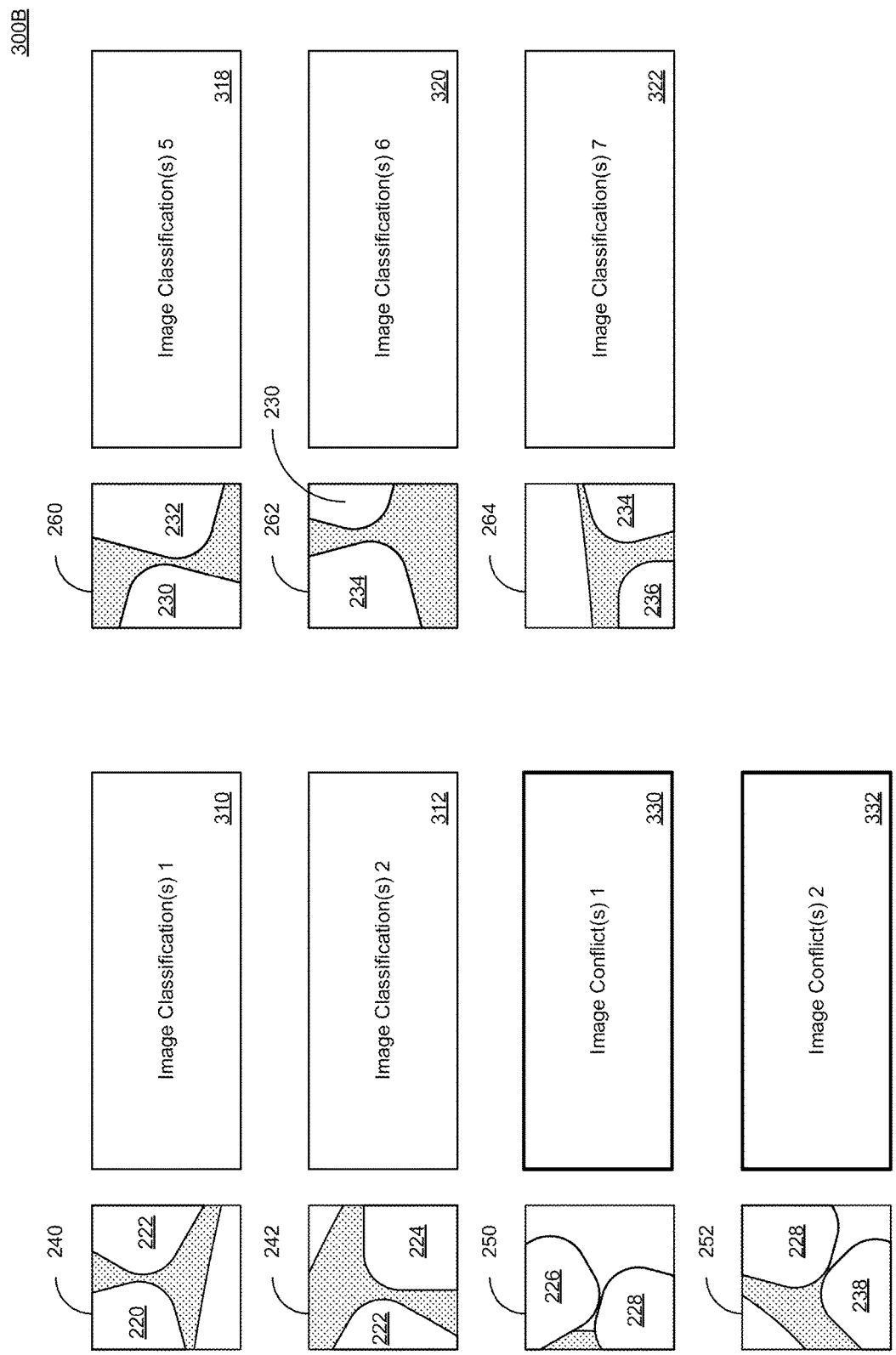
FIG. 3B illustrates an example a first user interface presentation based on an object layer of an object model, further to the example user interface presentation of FIG. 3A.

FIG. 3B illustrates an example a second user interface presentation based on an object layer of an object model, further to the example user interface presentation of FIG. 3A. As illustrated by way of example in FIG. 3B, a user interface presentation 300B can include the segments 240, 242, 250, 252, 260, 262 and 264 each including at least portions of various ones of the anatomical structures 220, 222, 224, 226, 228, 230, 232, 234, 236 and 238. The user interface presentation 300A can also include the diagnostic language portions 310, 312, 318, 320 and 322, and diagnostic language portions 330 and 332 including conflict presentations. At least one of the systems of FIGS. 4 and 5 can generate the user interface presentation 300B.

Figure 4:
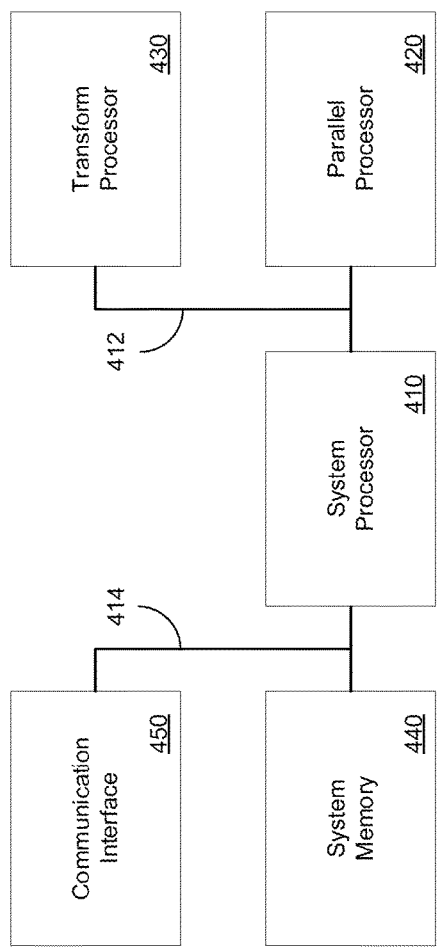
FIG. 4 illustrates a processing system, in accordance with present implementations.

FIG. 4 illustrates a processing system, in accordance with present implementations. As illustrated by way of example in FIG. 4, an example processing system 400 includes a system processor 410, a parallel processor 420, a transform processor 430, a system memory 440, and a communication interface 450. In some implementations, at least one of the example processing system 400 and the system processor 410 includes a processor bus 412 and a system bus 414.

The system processor 410 is operable to execute one or more instructions. In some implementations, the instructions are associated with at least one of the system memory 440 and the communication interface 450. In some implementations, the system processor 410 is an electronic processor, an integrated circuit, or the like including one or more of digital logic, analog logic, digital sensors, analog sensors, communication buses, volatile memory, nonvolatile memory, and the like. In some implementations, the system processor 410 includes but is not limited to, at least one microcontroller unit (MCU), microprocessor unit (MPU), central processing unit (CPU), graphics processing unit (GPU), physics processing unit (PPU), embedded controller (EC), or the like. In some implementations, the system processor 410 includes a memory operable to store or storing one or more instructions for operating components of the system processor 410 and operating components operably coupled to the system processor 410. In some implementations, the one or more instructions include at least one of firmware, software, hardware, operating systems, embedded operating systems, and the like.

The processor bus 412 is operable to communicate one or more instructions, signals, conditions, states, or the like between one or more of the system processor 410, the parallel processor 420, and the transform processor 430. In some implementations, the processor bus 412 includes one or more digital, analog, or like communication channels, lines, traces, or the like. It is to be understood that any electrical, electronic, or like devices, or components associated with the system bus 414 can also be associated with, integrated with, integrable with, supplemented by, complemented by, or the like, the system processor 410 or any component thereof.

The system bus 414 is operable to communicate one or more instructions, signals, conditions, states, or the like between one or more of the system processor 410, the system memory 440, and the communication interface 450. In some implementations, the system bus 414 includes one or more digital, analog, or like communication channels, lines, traces, or the like. It is to be understood that any electrical, electronic, or like devices, or components associated with the system bus 414 can also be associated with, integrated with, integrable with, supplemented by, complemented by, or the like, the system processor 410 or any component thereof.

The parallel processor 420 is operable to execute one or more instructions concurrently, simultaneously, or the like. In some implementations, the parallel processor 420 is operable to execute one or more instructions in a parallelized order in accordance with one or more parallelized instruction parameters. In some implementations, parallelized instruction parameters include one or more sets, groups, ranges, types, or the like, associated with various instructions. In some implementations, the parallel processor 420 includes one or more execution cores variously associated with various instructions. In some implementations, the parallel processor 420 includes one or more execution cores variously associated with various instruction types or the like. In some implementations, the parallel processor 420 is an electronic processor, an integrated circuit, or the like including one or more of digital logic, analog logic, communication buses, volatile memory, nonvolatile memory, and the like. In some implementations, the parallel processor 420 includes but is not limited to, at least one graphics processing unit (GPU), physics processing unit (PPU), embedded controller (EC), gate array, programmable gate array (PGA), field-programmable gate array (FPGA), application-specific integrated circuit (ASIC), or the like. It is to be understood that any electrical, electronic, or like devices, or components associated with the parallel processor 420 can also be associated with, integrated with, integrable with, supplemented by, complemented by, or the like, the system processor 410 or any component thereof.

Figure 5:
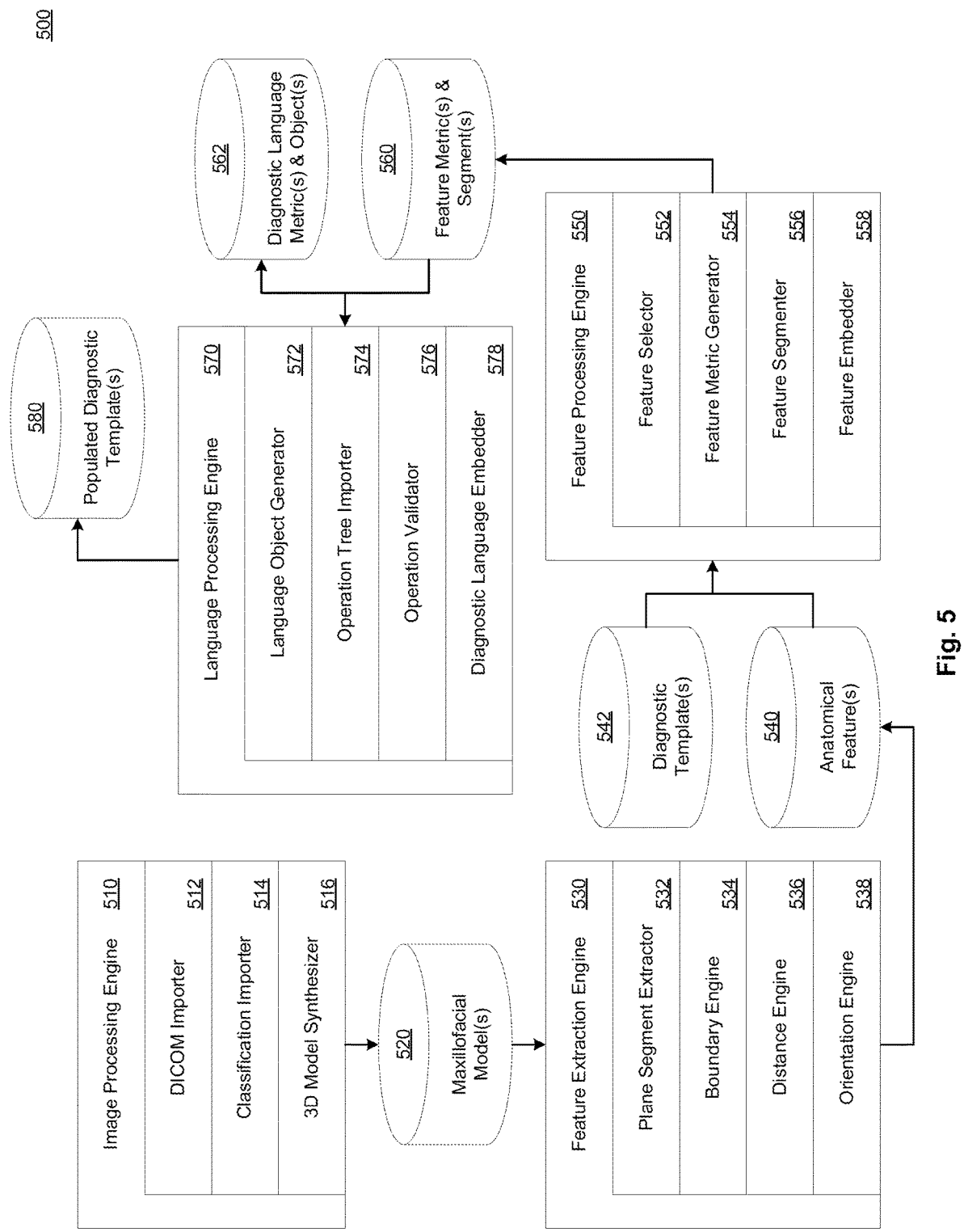
FIG. 5 illustrates a computing system, in accordance with present implementations.

In some implementations, various cores of the parallel processor 420 are associated with one or more parallelizable operations in accordance with one or more metrics, engines, models, and the like, of the example computing system of FIG. 5. As one example, parallelizable operations include processing portions of an image, video, waveform, audio waveform, processor thread, one or more layers of a learning model, one or more metrics of a learning model, one or more models of a learning system, and the like. In some implementations, a predetermined number or predetermined set of one or more particular cores of the parallel processor 420 are associated exclusively with one or more distinct sets of corresponding metrics, engines, models, and the like, of the example computing system of FIG. 5. As one example, a first core of the parallel processor 420 can be assigned to, associated with, configured to, fabricated to, or the like, execute one engine of the example computing system of FIG. 5. In this example, a second core of the parallel processor 420 can also be assigned to, associated with, configured to, fabricated to, or the like, execute another engine of the example computing system of FIG. 5. Thus, in some implementations, the parallel processor 420 is configured to parallelize execution across one or more metrics, engines, models, and the like, of the example computing system of FIG. 5. Similarly, in some implementations, a predetermined number or predetermined set of one or more particular cores of the parallel processor 420 are associated collectively with corresponding metrics, engines, models, and the like, of the example computing system of FIG. 5. As one example, a first plurality of cores of the parallel processor can be assigned to, associated with, configured to, fabricated to, or the like, execute one engine of the example computing system of FIG. 5. In this example, a second plurality of cores of the parallel processor can also be assigned to, associated with, configured to, fabricated to, or the like, execute another engine of the example computing system of FIG. 5. Thus, in some implementations, the parallel processor 420 is configured to parallelize execution within one or more metrics, engines, models, and the like, of the example computing system of FIG. 5.

The transform processor 430 is operable to execute one or more instructions associated with one or more predetermined transformation processes. As one example, transformation processes include Fourier transforms, matrix operations, calculus operations, combinatoric operations, trigonometric operations, geometric operations, encoding operations, decoding operations, compression operations, decompression operations, image processing operations, audio processing operations, and the like. In some implementations, the transform processor 430 is operable to execute one or more transformation processes in accordance with one or more transformation instruction parameters. In some implementations, transformation instruction parameters include one or more instructions associating the transform processor 430 with one or more predetermined transformation processes. In some implementations, the transform processor 430 includes one or more transformation processes. Alternatively, in some implementations, the transform processor 430 is a plurality of transform processor 430 associated with various predetermined transformation processes. Alternatively, in some implementations, the transform processor 430 includes a plurality of transformation processing cores each associated with, configured to execute, fabricated to execute, or the like, a predetermined transformation process. In some implementations, the parallel processor 420 is an electronic processor, an integrated circuit, or the like including one or more of digital logic, analog logic, communication buses, volatile memory, non-volatile memory, and the like. In some implementations, the parallel processor 420 includes but is not limited to, at least one graphics processing unit (GPU), physics processing unit (PPU), embedded controller (EC), gate array, programmable gate array (PGA), field-programmable gate array (FPGA), application-specific integrated circuit (ASIC), or the like. It is to be understood that any electrical, electronic, or like devices, or components associated with the transform processor 430 can also be associated with, integrated with, integrable with, supplemented by, complemented by, or the like, the system processor 410 or any component thereof.

In some implementations, the transform processor 430 is associated with one or more predetermined transform processes in accordance with one or more metrics, engines, models, and the like, of the example computing system of FIG. 5. In some implementations, a predetermined transform process of the transform processor 430 is associated with one or more corresponding metrics, engines, models, and the like, of the example computing system of FIG. 5. As one example, the transform processor 430 can be assigned to, associated with, configured to, fabricated to, or the like, execute one matrix operation associated with one or more engines, metrics, models, or the like, of the example computing system of FIG. 5. As another example, the transform processor 430 can alternatively be assigned to, associated with, configured to, fabricated to, or the like, execute another matrix operation associated with one or more engines, metrics, models, or the like, of the example computing system of FIG. 5. Thus, in some implementations, the transform processor 430 is configured to centralize, optimize, coordinate, or the like, execution of a transform process across one or more metrics, engines, models, and the like, of the example computing system of FIG. 5. In some implementations, the transform processor is fabricated to, configured to, or the like, execute a particular transform process with at least one of a minimum physical logic footprint, logic complexity, heat expenditure, heat generation, power consumption, and the like, with respect to at least one metrics, engines, models, and the like, of the example computing system of FIG. 5.

The system memory 440 is operable to store data associated with the example processing system 400. In some implementations, the system memory 440 includes ones or more hardware memory devices for storing binary data, digital data, or the like. In some implementations, the system memory 440 includes one or more electrical components, electronic components, programmable electronic components, reprogrammable electronic components, integrated circuits, semiconductor devices, flip flops, arithmetic units, or the like. In some implementations, the system memory 440 includes at least one of a non-volatile memory device, a solid-state memory device, a flash memory device, and a NAND memory device. In some implementations, the system memory 440 includes one or more addressable memory regions disposed on one or more physical memory arrays. In some implementations, a physical memory array includes a NAND gate array disposed on a particular semiconductor device, integrated circuit device, printed circuit board device, and the like.

The communication interface 450 is operable to communicatively couple the system processor 410 to an external device. In some implementations, an external device includes but is not limited to a smartphone, mobile device, wearable mobile device, tablet computer, desktop computer, laptop computer, cloud server, local server, and the like. In some implementations, the communication interface 450 is operable to communicate one or more instructions, signals, conditions, states, or the like between one or more of the system processor 410 and the external device. In some implementations, the communication interface 450 includes one or more digital, analog, or like communication channels, lines, traces, or the like. As one example, the communication interface 450 is or includes at least one serial or parallel communication line among multiple communication lines of a communication interface. In some implementations, the communication interface 450 is or includes one or more wireless communication devices, systems, protocols, interfaces, or the like. In some implementations, the communication interface 450 includes one or more logical or electronic devices including but not limited to integrated circuits, logic gates, flip flops, gate arrays, programmable gate arrays, and the like. In some implementations, the communication interface 450 includes ones or more telecommunication devices including but not limited to antennas, transceivers, packetizers, wired interface ports, and the like. It is to be understood that any electrical, electronic, or like devices, or components associated with the communication interface 450 can also be associated with, integrated with, integrable with, replaced by, supplemented by, complemented by, or the like, the system processor 410 or any component thereof.

FIG. 5 illustrates a computing system, in accordance with present implementations. As illustrated by way of example in FIG. 5, a computing system 500 can include an image processing engine 510, a maxillofacial model database 520, a feature extraction engine 530, an anatomical feature database 540, a diagnostic template database 542, a feature processing engine 550, a feature metric and segments database 560, a diagnostic language metrics and objects database 562, a language processing engine 570, and a populated diagnostic template database 580.

The image processing engine 510 is operable to generate at least one three-dimensional (3D) model based on one or more two-dimensional (2D) images. In some implementations, the image processing engine 510 includes at least one of a DICOM importer 512, a classification importer 514, and a three-dimensional model synthesizer 516.

The DICOM importer 512 is operable to obtain one or more images in a DICOM format or the like. In some implementations, the DICOM importer 512 is operable to obtain one or more images along one or more axes or planes corresponding to a patient facial region, dentition region, oral region, maxillofacial region, or the like. It is to be understood that the DICOM importer 512 can obtain and process images in formats other than DICOM images, including but not limited to PNG, SVG, BMP, JPG, JPEG, JPEG2000, TIFF, and the like.

The classification importer 514 is operable to obtain one or more classifications associated with one or more of the 2D images obtained by the DICOM importer 512. In some implementations, classifications include one or more tags, associations, flag, bits, strings, or the like associated with a corresponding one or more of the 2D images and indicating a characteristic of those 2D images. As one example, a classification can include an indication that a particular 2D image is associated with a particular age, demographic, gender, health condition, or the like. In some implementations, the 2D images can be associated with more than one classification, that as a group can identify a 2D image classification with increased granularity. In this example, a group of 2D images can be classified as associated with a gender classification indicating a female gender, and an age classification indicating 10 years of age. As another example, a group of 2D images can be classified as associated with an individual from whom the 2D images are derived, associated, or the like. Thus, all 2D images associated with both of these classifications can be presumed to have features corresponding to 10 year old females. Thus, in some implementations, a composite 3D model based on one more classifications can be generated. In some implementations, the classification importer 514 can import 2D images associated with one or more classifications. In some implementations, the classification importer 514 can import classifications independently of 2D images and associate classifications with various 2D images in accordance with a prompt or other user input.

The three-dimensional (3D) model synthesizer 516 is operable to generate at least one 3D model corresponding to one or more 2D images. In some implementations, the 3D model synthesizer 516 is operable to filter, select, block, or the like, one or more 2D images based on one or more classifications. As one example, the 3D model synthesizer 516 can select only 2D images associated with a particular classification or particular set of classifications. Thus, the 3D model synthesizer 516 can select, for example, only 2D images associated with a particular individual or a particular subset of classifications. As one example, a subset of classifications can be applied to select only 2D images associated with females between ages 6 and 12. As another example, a subset of classifications can be applied to select only 2D images associated with males between ages 45 and 65. In some implementations, the 3D model synthesizer 516 generates a 3D model based on the selected 2D images, resulting in a 3D model corresponding to at least one of the 2D selected 2D images. In some implementations, the 3D model includes one or more 3D features corresponding to one or more of the selected 2D images. Thus, the 3D synthesizer 516 is operable to generate a 3D model associated with 2D images of a particular individual, and to generate a 3D model associated with 2D images corresponding to individuals sharing one or more particular classifications.

The maxillofacial model database 520 includes at least one maxillofacial extraction model associated with one or more types of maxillofacial structures. In some implementations, maxillofacial structures include one or more structures, regions, or the like associated with a maxillofacial area of a skull, and the like. As one example, a maxillofacial structure can include a maxilla or other bone structure. In some implementations, the maxillofacial model database 520 includes one or more maxillofacial metrics associated with identifying shape, orientation, and location of maxillofacial structures of the patient associated with the 3D model.

The feature extraction engine 530 can identify one or more characteristics of one or more features, objects, or the like within a model or an object layer. The feature extraction engine can include a plane segment extractor 532, a boundary engine 534, a distance engine 536, and an orientation engine 538. The plane segment extractor 532 can extract a plane corresponding to an object layer from the 3D model or a stack of 2D image layers corresponding to the 3D model. The boundary engine 534 can identify one or more boundaries of one or more maxillofacial structures and one or more anatomical features. The distance engine 536 can generate one or more distance metrics or values corresponding to one or more anatomical features in the object layer. The distance engine 536 can generate distances at least in accordance with FIG. 2A. The orientation engine 538 can determine one or more spatial characteristics of one or more anatomical features. As one example, the orientation engine 538 can determine a rotation of a tooth within a maxillofacial structure.

The anatomical feature database 540 can store one or more anatomical features extracted by the feature extraction engine. The diagnostic template database 542 can store one or more diagnostic templates to generate one or more user interface presentations. The diagnostic templates can correspond to those of FIGS. 3A and 3B.

The feature processing engine 550 can generate one or more characteristics associated with one or more anatomical features, and can perform one or more operations with respect to individual anatomical features or groups of anatomical features. The feature processing engine 550 can include a feature selector 552, a feature metric generator 554, a feature segmenter 556, and a feature embedder 558. The feature selector 552 can identify one or more features for further processing. The feature metric generator 554 can generate one or more metrics associated with one or more characteristics of the anatomical feature, either individually, or with respect to other anatomical features, for example. The feature segmenter 556 can generate one or more segments associated with one or more proximate anatomical features. The feature segmenter 556 can generate one or more segments based on one or more feature metrics, including, for example, feature metrics indicating a particular distance between two anatomical features. The feature embedder 558 can embed one or more segments into a corresponding diagnostic template.

The feature metric and segments database 560 can store one or more feature metrics and segments. The feature metrics can be associated with their corresponding particular segments based on the associated between each of the feature metrics and segments with particular anatomical features in the segments and described by the feature metrics. The segments can correspond at least to the segments of FIG. 2B. The diagnostic language metrics and objects database 562 can store diagnostic language objects. The diagnostic language objects can include, for example, text, images, and formatting guidelines therefor. The diagnostic language objects can be associated with medical, surgical, or like operations, modifications or the like, performable on or with respect to one or more anatomical features of a particular segment.

The language processing engine 570 can identify one or more relationships between one or more diagnostic language objects, and can modify one or more diagnostic templates and their associated segment or segments in response to the identified relationships. The language processing engine 570 can include a language object generator 572, an operation tree importer 574, an operation validator 576, and a diagnostic language embedder 578. The language object generator 572 can generate a diagnostic language object associated with a particular segment, based on the diagnostic language metrics and objects. The operation tree importer 572 can obtain at least one tree data structure corresponding to relationships between particular operations, modifications or the like, performable on or with respect to one or more anatomical features of a particular segment. The operation validator 576 can determine whether two or more diagnostic language objects associated with respective segments are in conflict. A conflict may be determined by determining that two or more diagnostic language objects are associated with nodes in different subtrees of a tree structure. The tree structure can include a predetermined tree indicating procedures that are related, interdependent, or compatible with each other. The diagnostic language embedder 578 can embed one or more diagnostic language objects into a diagnostic template with respect to the corresponding segment. The diagnostic language embedder 578 can also modify a diagnostic language object based on a determination that a conflict exists.

The populated diagnostic template database 580 can store diagnostic user interface presentation objects including diagnostic templates with embedded segments. Each diagnostic user interface presentation object can be associated with a particular scan of an object layer of a particular patient. The diagnostic user interface presentation objects can correspond at least partially to FIGS. 3A and 3B.

Figure 6:
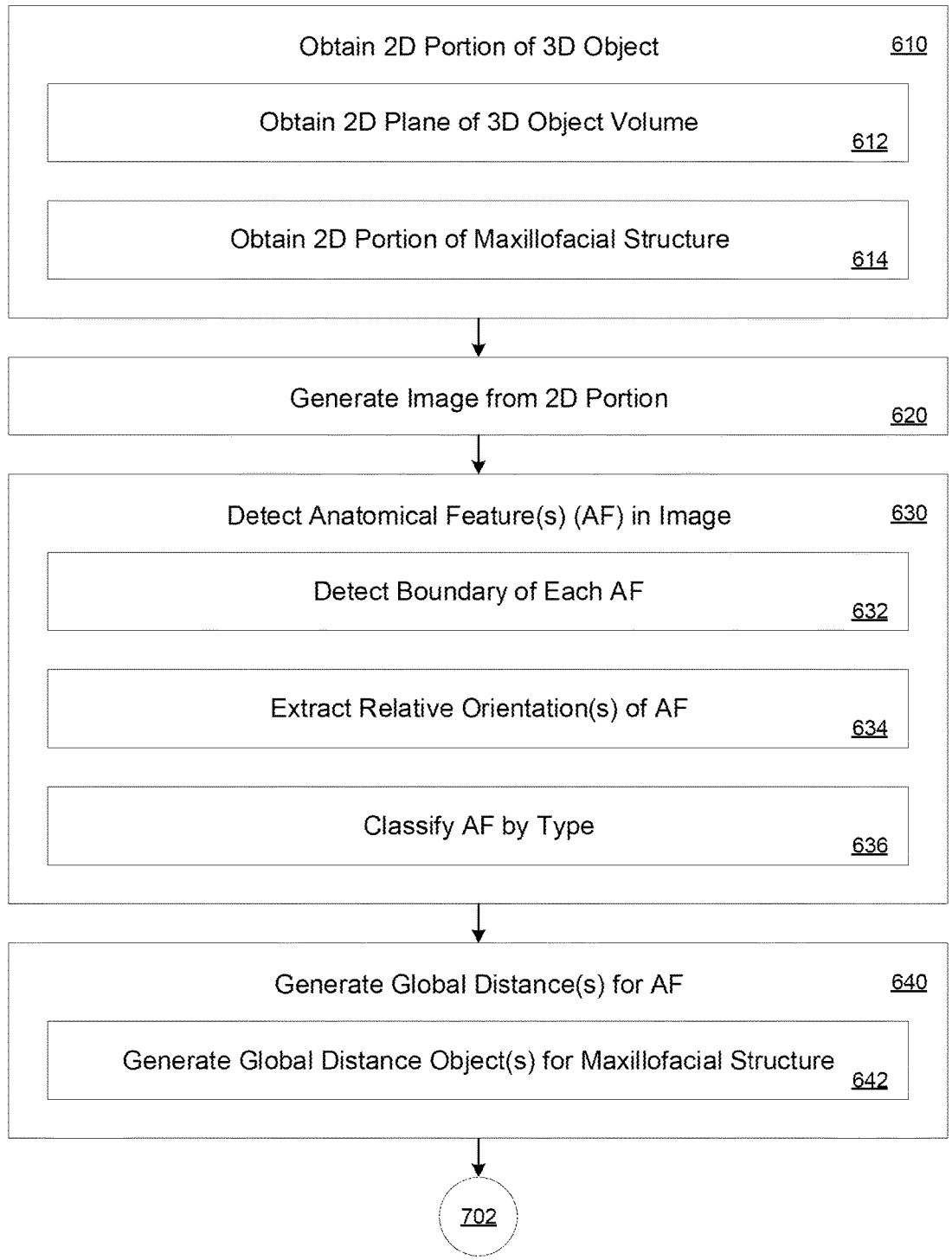
FIG. 6 illustrates an example method of generating a diagnostic model and user interface presentation based on individual anatomical features, in accordance with present implementations.

FIG. 6 illustrates an example method of generating a diagnostic model and user interface presentation based on individual anatomical features, in accordance with present implementations. At least one of the systems 400 and 500 can perform method 600 according to present implementations. The method 600 can begin at step 610.

At step 610, the method can obtain a two-dimensional (2D) portion of a three-dimensional (3D) object. Step 610 can include at least one of steps 612 and 614. At step 612, the method can obtain a 2D plane of a 3D object volume. At step 614, the method can obtain a 2D portion of a maxillofacial structure. The method 600 can then continue to step 620.

At step 620, the method can generate an image from the 2D portion. The method 600 can then continue to step 630.

At step 630, the method can detect one or more anatomical features in the image. Step 630 can include at least one of steps 632, 634 and 636. At step 632, the method can detect a boundary associated with each anatomical feature. At step 634, the method can extract a relative orientation of one or more anatomical features. At step 636, the method can classify one or more anatomical features by type. The method 600 can then continue to step 640.

At step 640, the method can generate at least one global distance associated with at least one anatomical feature. Step 640 can include step 642. At step 642, the method can generate at least one global distance object corresponding to a maxillofacial structure. The method 600 can then continue to step 702.

Figure 7:
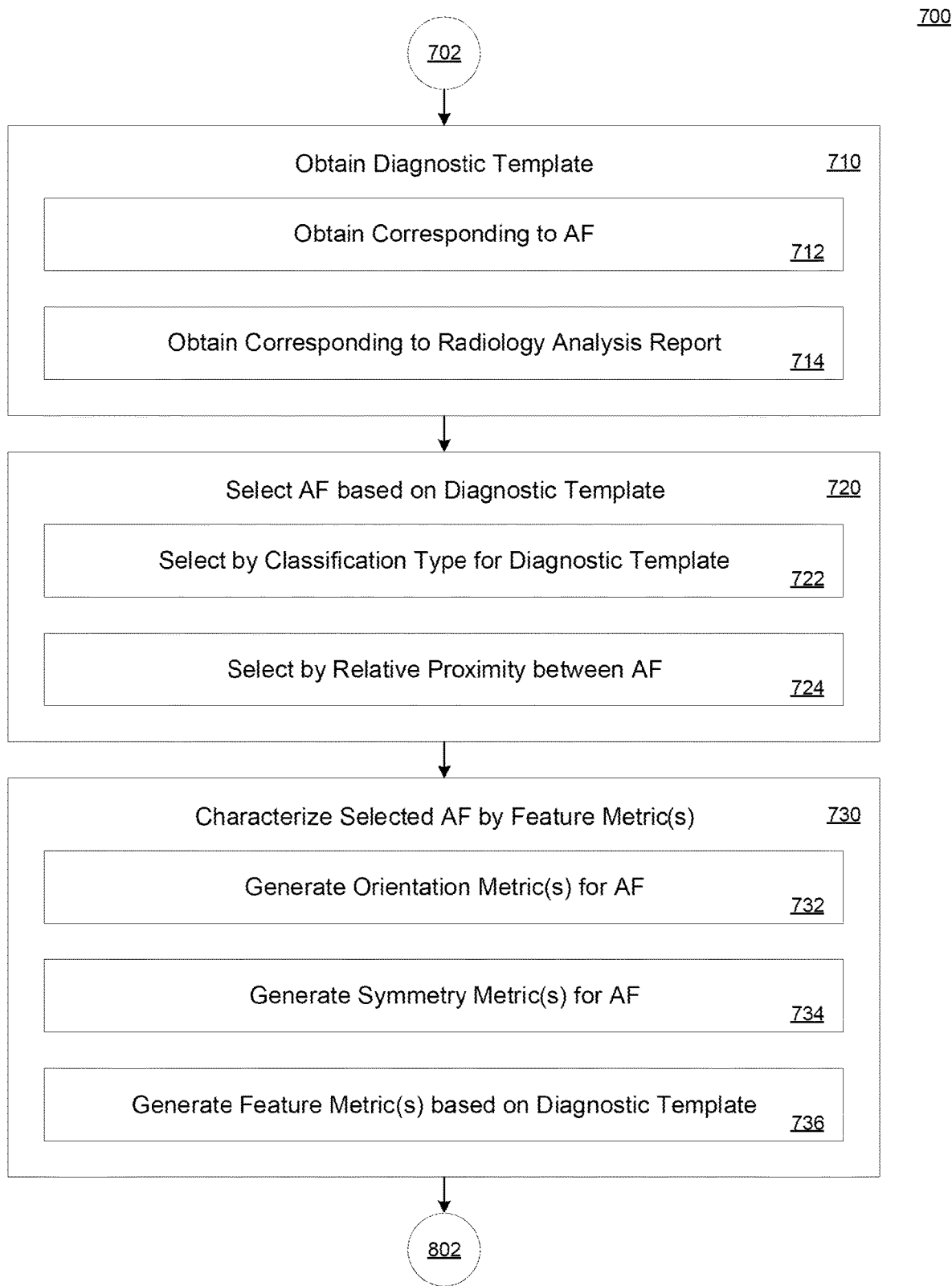
FIG. 7 illustrates an example method of generating a diagnostic model and user interface presentation based on individual anatomical features further to the example method of FIG. 6.

FIG. 7 illustrates an example method of generating a diagnostic model and user interface presentation based on individual anatomical features further to the example method of FIG. 6. At least one of the systems 400 and 500 can perform method 700 according to present implementations. The method 700 can begin at step 702. The method 700 can then continue to step 710.

At step 710, the method can obtain at least one diagnostic template. The diagnostic template can correspond to at least a portion of an object presentable at a graphical user interface. Step 710 can include at least one of steps 712 and 714. At step 712, the method can obtain a diagnostic template corresponding to at least one anatomical feature. At step 714, the method can obtain a diagnostic template corresponding to a radiology analysis report. The method 700 can then continue to step 720.

At step 720, the method can select at least one anatomical feature based on the diagnostic template. Step 720 can include at least one of steps 722 and 724. At step 722, the method can select an anatomical feature based at least partially on a classification type associated with the anatomical feature and at least a portion of the diagnostic template. At step 724, the method can select a diagnostic template based at least partially on a proximity between anatomical features. The method 700 can then continue to step 730.

At step 730, the method can characterize at least one selected anatomical feature based on at least one feature metric corresponding to the anatomical feature. Step 730 can include at least one of steps 732, 734 and 736. At step 732, the method can generate at least one orientation metric corresponding to at least one anatomical feature. At step 734, the method can generate at lest one symmetry metric corresponding to at least one anatomical feature. At step 736, the method can generate one or more feature metrics based at least partially on the diagnostic template. The method 700 can then continue to step 802.

Figure 8:
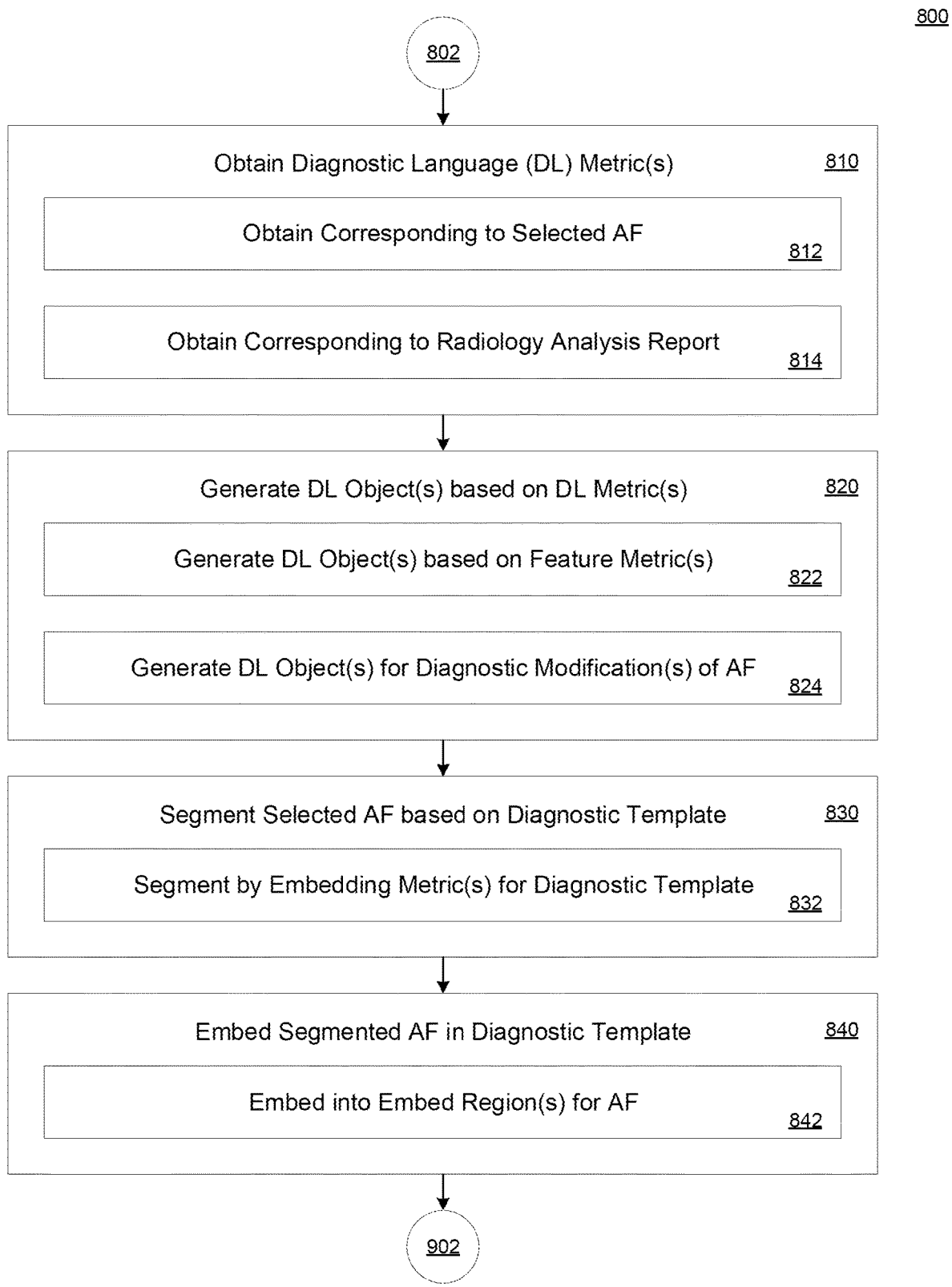
FIG. 8 illustrates an example method of generating a diagnostic model and user interface presentation based on individual anatomical features further to the example method of FIG. 7.

FIG. 8 illustrates an example method of generating a diagnostic model and user interface presentation based on individual anatomical features further to the example method of FIG. 7. At least one of the systems 400 and 500 can perform method 800 according to present implementations. The method 800 can begin at step 802. The method 800 can then continue to step 810.

At step 810, the method can obtain one or more diagnostic language metrics. Diagnostic language metrics can include text objects or numerical objects, for example, corresponding to particular anatomical features or reports. Step 810 can include at least one of steps 812 and 814. At step 812, the method can obtain diagnostic language metrics corresponding to at least one anatomical feature. At step 814, the method can obtain diagnostic language metrics corresponding to at least one radiology analysis report. The method 800 can then continue to step 820.

At step 820, the method can generate one or more diagnostic language objects based on diagnostic language metrics. Step 820 can include at least one of steps 822 and 824. At step 822, the method can generate one or more diagnostic language objects based at least partially on one or more feature metrics. Feature metrics can include, text objects or numerical objects, for example, associated with at least a portion of an anatomical feature. At step 824, the method can generate one or more diagnostic language objects corresponding to a diagnostic modification of an anatomical feature. A diagnostic modification can include a modeled change to an anatomical feature. As one example, an anatomical feature can be a tooth having an orientation causing contact with another tooth, and a modeled change can include an orientation of the tooth or a movement of the tooth to eliminate the contact. The method 800 can then continue to step 830.

At step 830, the method can segment at least one selected anatomical feature based on the diagnostic template. Step 830 can include step 832. At step 832, the method can segment at least one selected anatomical feature based on at least one embedding metric associated with a diagnostic template. The embedding metric can correspond to at least one restriction or constraining on embedding an anatomical feature in the diagnostic template. Constraints can include, for example, a size, shape, or colorization of a portion of an image corresponding to the anatomical feature. The method 800 can then continue to step 840.

At step 840, the method can embed the segmented anatomical feature in the diagnostic template. Step 840 can include step 842. At step 842, the method can embed the segmented anatomical feature into a corresponding embed region of a diagnostic template associated with the anatomical feature. The method 800 can then continue to step 902.

Figure 9:
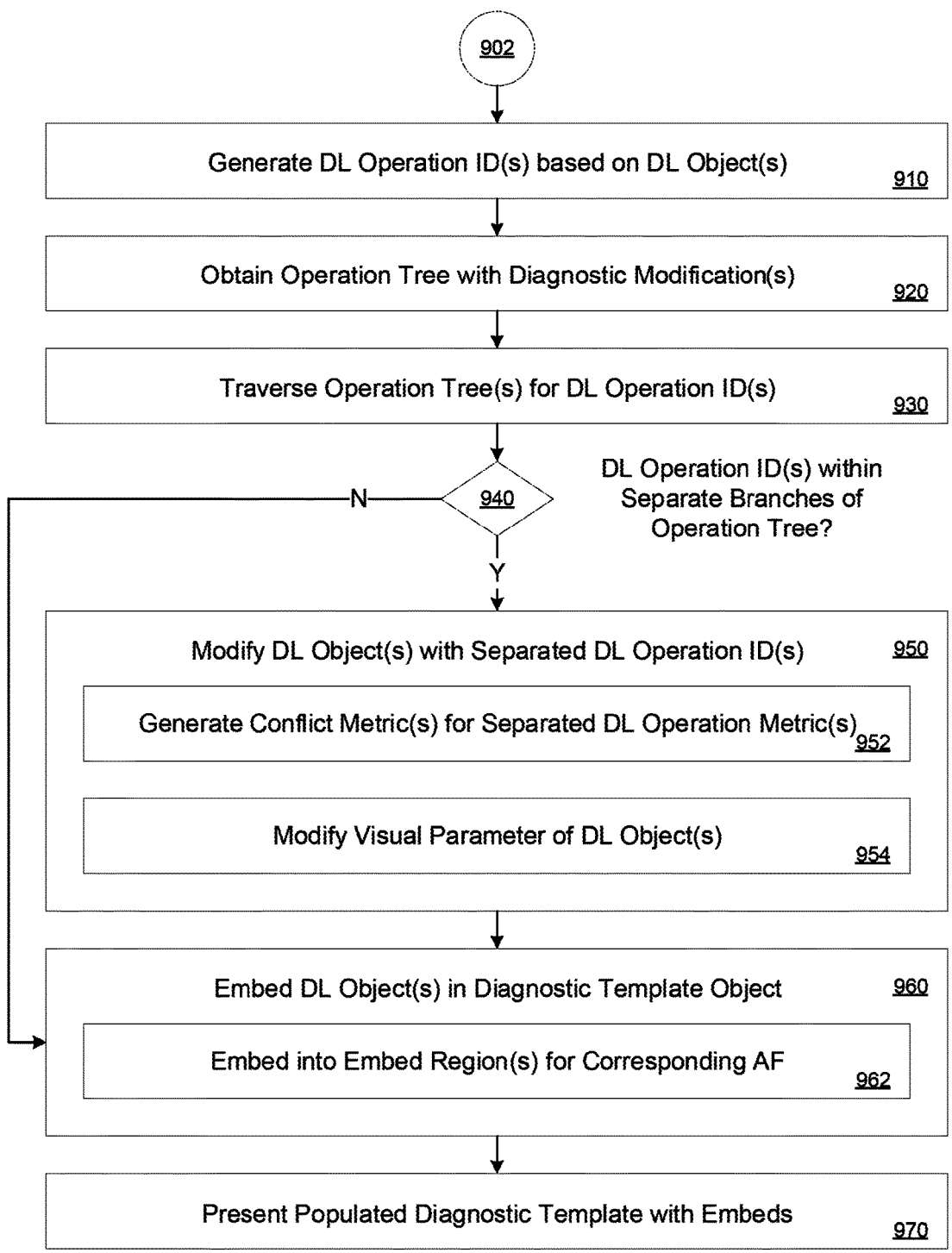
FIG. 9 illustrates an example method of generating a diagnostic model and user interface presentation based on individual anatomical features further to the example method of FIG. 8.

FIG. 9 illustrates an example method of generating a diagnostic model and user interface presentation based on individual anatomical features further to the example method of FIG. 8. At least one of the systems 400 and 500 can perform method 900 according to present implementations. The method 900 can begin at step 902. The method 900 can then continue to step 910.

At step 910, the method can generate at least one diagnostic language operation based on at least one corresponding diagnostic language object. The method 900 can then continue to step 920.

At step 920, the method can obtain at least one operation tree including one or more diagnostic modifications. The method 900 can then continue to step 930.

At step 930, the method can traverse the operation tree to identify one or more operation identifiers associated with one or more diagnostic modifications associated with one or more segmented anatomical features. The method 900 can then continue to step 940.

At step 940, the method can determine whether any operation identifiers are within separate branches of an operation tree structure. As one example, operation identifiers in separate branches may be associated with incompatible diagnostic modifications. Incompatible diagnostic modifications can include dental procedures that cannot be performed concurrently due to biological or medical restrictions. In accordance with a determination that operation identifiers are within separate branches of an operation tree structure, the method 900 can continue to step 950. Alternatively, in accordance with a determination that operation identifiers are not within separate branches of an operation tree structure, the method 900 can continue to step 960.

At step 950, the method can modify one or more diagnostic language objects associated with separated diagnostic operation identifiers. Step 950 can include at least one of steps 952 and 954. At step 952, the method can generate one or more conflict metrics corresponding to one or more separated diagnostic language objects. At step 954, the method can modify at least one visual parameter of at least one diagnostic language object. A visual parameter can correspond to a color, a highlight, a line thickness, a line color, or a text characteristic, for example, corresponding to a diagnostic object. The method 900 can then continue to step 960.

At step 960, the method can embed at least one diagnostic language object in a diagnostic template object. Step 960 can include step 962. At step 962, the method can embed the diagnostic language object into an embed region corresponding to an anatomical feature. The diagnostic language object can include a description of the anatomical features, a diagnostic modification associated with the anatomical feature, and a conflict metric or object based thereon, for example. The method 900 can then continue to step 970.

At step 970, the method can present a populated diagnostic template including one or more embedded objects at one or more embed regions thereof. The method 900 can end at step 970.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

The foregoing description of illustrative implementations has been presented for purposes of illustration and of description. It is not intended to be exhaustive or limiting with respect to the precise form disclosed, and modifications and variations are possible in light of the above teachings or may be acquired from practice of the disclosed implementations. It is intended that the scope of the invention be defined by the claims appended hereto and their equivalents.

What is claimed is:

1. A method of generating a diagnostic model and user interface presentation based on individual anatomical features, the method comprising:
    generating a distance associated with a subset of anatomical features;
    characterizing the anatomical features based on one or more feature metrics;
    generating one or more diagnostic language objects associated with the anatomical features based on one or more diagnostic language metrics;
    segmenting one or more of the anatomical features based on a diagnostic template for the user interface presentation;
    embedding one or more of the segments of the anatomical features in the diagnostic template; and
    modifying at least one of the diagnostic language objects, in response to a determination that the diagnostic language object is associated with a separate branch of a tree from another one of the diagnostic language objects such that the embedded diagnostic template respects relationships between diagnostic language objects.

2. The method of claim 1, further comprising:
    traversing the tree based on the diagnostic language objects.

3. The method of claim 1, further comprising:
    present, at a user interface, the diagnostic template including the embedded segments.

4. The method of claim 1, further comprising:
    obtaining the diagnostic template corresponding to the anatomical features.

5. The method of claim 1, further comprising:
    detecting the anatomical features in an image.

6. The method of claim 5, further comprising:
    classifying the anatomical images by a type.

7. The method of claim 1, wherein the diagnostic language objects are generated based on feature metrics.

8. The method of claim 1, wherein when modifying the diagnostic language objects, a visual parameter of the diagnostic language objects is modified.

9. A system of generating a diagnostic model and user interface presentation based on individual anatomical features, the system comprising:
    an image processing engine operable by a processor to generate a distance associated with a subset of anatomical features, characterizing the anatomical features based on one or more feature metrics, and generate one or more diagnostic language objects associated with the anatomical features based on one or more diagnostic language metrics; and an feature processing engine operable by a processor to segment one or more of the anatomical features based on a diagnostic template for the user interface presentation, embed one or more of the segments of the anatomical features in the diagnostic template, and modify at least one of the diagnostic language objects, in response to a determination that the diagnostic language object is associated with a separate branch of a tree from another one of the diagnostic language objects such that the embedded diagnostic template respects relationships between diagnostic language objects.

10. The system of claim 9, further comprises a language processing engine operable by a processor to traverse the tree and determine whether the diagnostic language object is associated with a separate branch of the tree.

11. The system of claim 9, wherein the image processing engine is further operable by the processor to present, at a user interface, the diagnostic template including the embedded segments.

12. The system of claim 9, wherein the feature processing engine is further operable by the processor to obtain the diagnostic template corresponding to the anatomical features.

13. The system of claim 9, wherein the feature processing engine is further operable by the processor to detect the anatomical features in an image.

14. A computer readable medium comprising non-transitory computer readable media including one or more instructions stored thereon and executable by a processor to:

generate, by the processor, a distance associated with a subset of anatomical features;

characterize, by the processor, the anatomical features based on one or more feature metrics;

generate, by the processor, one or more diagnostic language objects associated with the anatomical features based on one or more diagnostic language metrics;

segment, by the processor, one or more of the anatomical features based on a diagnostic template;

embed, by the processor, one or more of the segments of the anatomical features in the diagnostic template for the user interface presentation; and modify, by the processor, at least one of the diagnostic language objects, in response to a determination that the diagnostic language object is associated with a separate branch of a tree from another one of the diagnostic language objects such that the embedded diagnostic template respects relationships between diagnostic language objects.

15. The computer readable medium of claim 14, the computer readable medium further includes one or more instructions executable by processor to:

traverse the tree based on the diagnostic language objects.

16. The computer readable medium of claim 14, the computer readable medium further includes one or more instructions executable by processor to:

present, at a user interface, the diagnostic template including the embedded segments.

17. The computer readable medium of claim 14, the computer readable medium further includes one or more instructions executable by processor to:

obtain the diagnostic template corresponding to the anatomical features.

18. The computer readable medium of claim 14, the computer readable medium further includes one or more instructions executable by processor to:

detect the anatomical features in an image.

19. The computer readable medium of claim 14, the computer readable medium further includes one or more instructions executable by processor to:

classify the anatomical images by a type.

20. The computer readable medium of claim 14, wherein when modifying the diagnostic language objects, a visual parameter of the diagnostic language objects is modified.

* * * * *